United States Patent [19]

Phillips et al.

[11] Patent Number: 4,530,695

[45] Date of Patent: Jul. 23, 1985

[54] INJECTOR

[75] Inventors: Ian R. Phillips, Killara; Mervyn F. Reynolds, Balgowlah; Robert H. Lodge, Wheeler Heights, all of Australia

[73] Assignee: N.J. Phillips Pty. Limited, New South Wales, Australia

[21] Appl. No.: 563,030

[22] Filed: Dec. 19, 1983

[30] Foreign Application Priority Data

Dec. 31, 1982 [AU] Australia ............................ PF7465

[51] Int. Cl.³ .............................................. A61M 5/00
[52] U.S. Cl. ..................................... 604/184; 604/134
[58] Field of Search .............. 604/184, 186, 134, 135, 604/187, 137

[56] References Cited

U.S. PATENT DOCUMENTS

| 2,821,193 | 1/1958 | Ziherl et al. | 604/184 |
| 3,400,716 | 9/1968 | Schultz | 604/184 |
| 3,494,358 | 2/1970 | Fehlis et al. | 604/137 |
| 4,403,989 | 9/1983 | Christensen et al. | 604/137 |

Primary Examiner—John D. Yasko
Attorney, Agent, or Firm—Ladas & Parry

[57] ABSTRACT

An injector to inject liquid into an animal, said injector being of generally cylindrical configuration and having a pre-loadable piston and cylinder which when operated eject liquid through a needle of the injector, said injector having a trigger movably mounted at one end, which trigger selectively permits relative movement of the piston and cylinder to eject liquid from within the injector.

11 Claims, 2 Drawing Figures

INJECTOR

The present invention relates to injecting or drenching apparatus used to despense a required dose to an animal.

Known injecting apparatus requires the use of a trigger or similar arrangement to which the user must apply a force to operate the device in order to deliver a desired dose unit to an animal. Accordingly, these known devices require two actions, firstly the apparatus must be maintained at a desired location relative to the animal, and secondly the user must operate the device in order to deliver the dose to the animal as for example, described in U.S. Pat. No. 4,403,989.

It is the object of the present invention to overcome or substantially ameliorate the above disadvantages by providing an injector which is operated by a single action.

There is disclosed herein an injector comprising, an elongated hollow body, an interacting piston and cylinder mounted within the body and co-operating to provide a variable volume chamber, a first passage extending from said chamber to one end of said body to communicate with an injection needle, a second passage extending from said chamber toward the other end of said body and to be connected to a reservoir of liquid to be delivered by said injector, valve means restricting said liquid to move through said injector from said second passage to said first passage, spring means biasing said piston and cylinder to move relative to each other to minimise the volume of said chamber, retaining means to selectively prevent relative movement of said piston and cylinder to minimise said volume, and trigger release means movably mounted at said one end of said body and operatively associated with said retaining means to operate same to permit relative movement between said piston and cylinder to thereby eject liquid through said first passage.

A preferred form of the present invention will now be described by way of example with reference to the accompanying drawings wherein.

Figure 1:
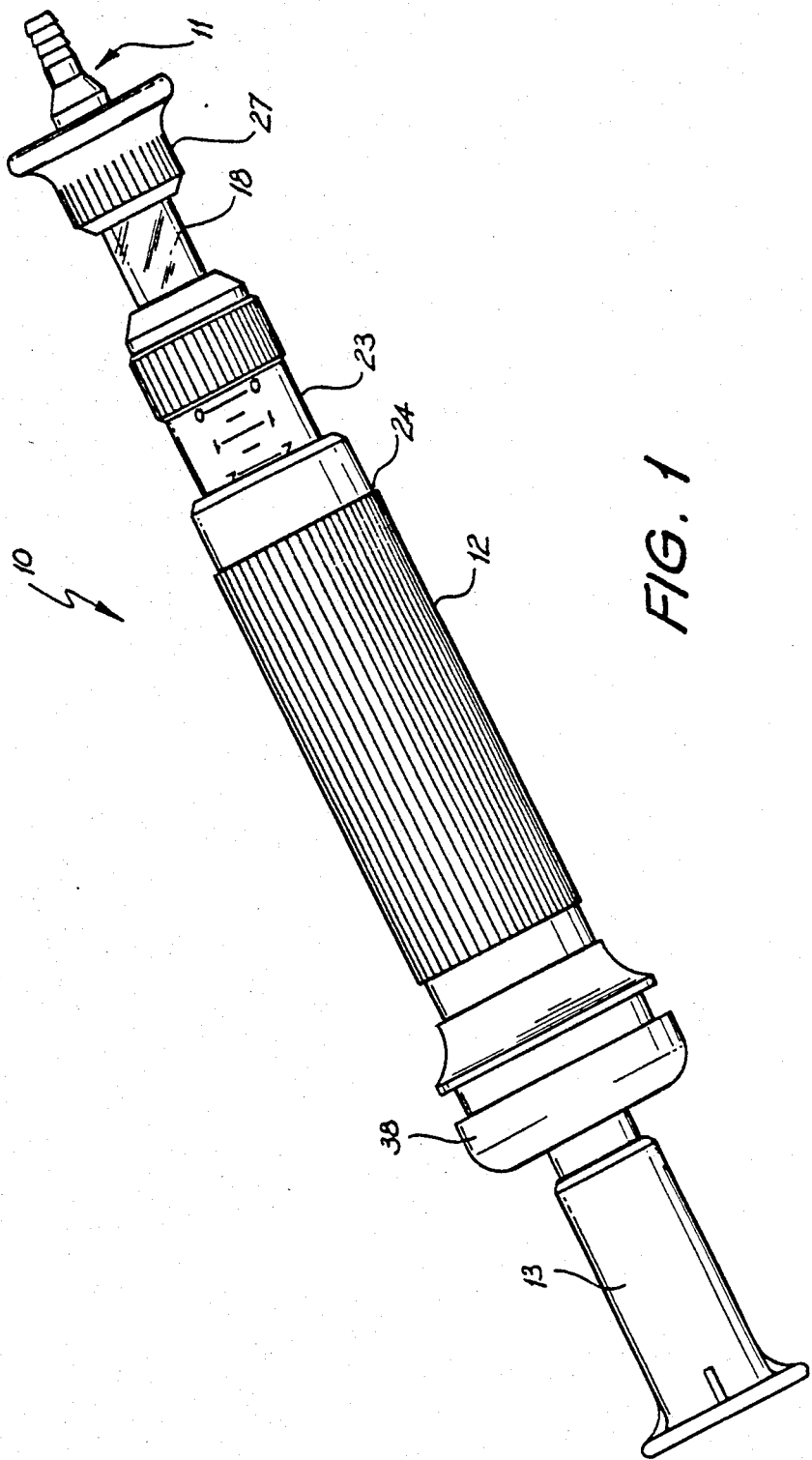
FIG. 1 is a schematic side elevation of a dose or injector apparatus.
Figure 2:
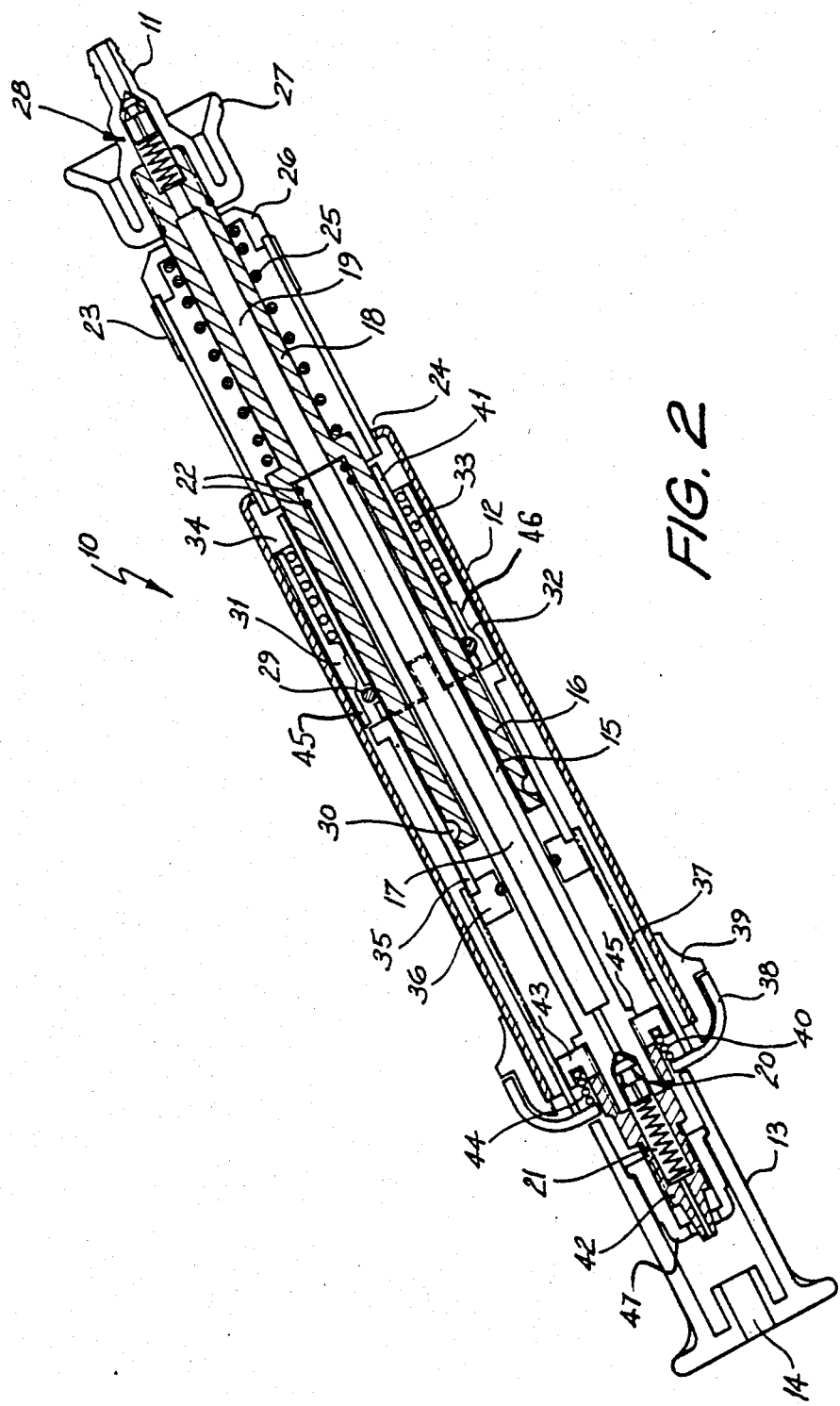
FIG. 2 is a schematic section side elevation of the apparatus of FIG. 1.

In FIG. 1 there is schematically depicted a drenching or injecting device 10 which is adapted to deliver a predetermined dose to an animal. The device 10 has a spigot connector 11 adapted to be attached to a flexible line which leads to a reservoir of drench. The device 10 further has an outer cylindrical casing 12 which is gripped by a user in applying the device to an animal. One end of the device 10 receives a needle (not depicted), which needle is protected by means of a retractable shroud 13 which is provided with a passage 14 through which the needle will project in use. The shroud 13 is slidably supported via an adaptor 47 slidably engaging the needle support 42.

Mounted within the casing 12 is an interacting piston 15 and cylinder 16 which cooperate to define a variable volume working space which draws in drench through the spigot connector 11 and delivers the drench through the needle at the other end. The piston 15 is elongated and hollow so as to provide a longitudinal passage 17 which communicates with the internal space defined by the cylinder 16. The cylinder 16 has extending from it a conduit 18 providing a passage 19 which provides for communication between the spigot connector 11 and the space defined by the cylinder. The passage 17 communicates with a one-way valve assembly 20 and passage 21 which delivers drench to the needle. Located between the piston 15 and the internal surface of the cylinder 16 are seals 22 which allow for sliding relative movement between the piston 15 and cylinder 16. It should be appreciated that the piston is fixed to the casing 12 while the cylinder is selectively movable relative thereto.

Located around the conduit 18 is a rotatable sleeve 23 which threadably engages the casing 12 by means of a threaded flange 24. The sleeve 23 is rotatable about its longitudinal axis and is provided with graduation marks indicating dosage volumes. Encompassing the conduit 18 is a spring 25 which abuts the cylinder 16 and an end flange 26 of the sleeve 23 thereby biasing the cylinder 16 to move in a leftward direction towards the needle, and minimising the volume of the working space defined by the piston 15 and cylinder 16.

Accordingly the variable volume defined by the interacting piston 15 and cylinder 16 is at a minimum when the piston 15 and cylinder 16 are free for relative movement. The right hand end of the conduit 18 is equipped with a knob 27 which is gripped by a user and retracted to thereby cause the cyliner 16 to move relative to the piston 15 to increase the variable volume defined thereby. Accordingly as the volume increases drench is drawn in through the one-way valve assembly 28 and spigot connector 11, which upon the cylinder 16 being again released for movement, the volume decreases forcing the drench out through the one-way valve assembly 20. The knob 27 abuts the sleeve 23 to regulate the volume delivered.

Upon the cylinder 16 being moved relative to the piston 15 by a user pulling the knob 27, the piston 15 and cylinder 16 are prevented from relative movement by means of engagement of a plurality of balls 29 being positioned within an annular recess 30 formed in the cylinder 16. Encompassing the balls 29 is a release member 31 which is in the form of a sleeve having a frusto conical surface 32 to engage the balls 29. The release member 31 is biased under the influence of the spring 33 to force the balls 29 into engagement within the recess 30 by the spring 33 abutting a spacer 34 and the release member 31. The surface 32 joins a radially outer cylindrical surface 45 which allows the balls 29 to move radially outward from within the recess 30 to release the cylinder 16, while the radially inward cylindrical surface 46 retains the balls 29 within the recess 30.

The balls 29 are retained in position by a cage 46 which has a plurality of angularly spaced holes 47 which receive the balls 29.

The cylinder 16 is released from its position fixed by the balls 29, by a sleeve 35 which has an end flange 36 adapted to engage the adjacent extremity of the release member 31 to thereby move the release member 31 to a position allowing radial outward movement of the balls 29 from within the recess 30. The sleeve 35 is attached to a support member 36 which in turn is attached to an actuating member 37 abutting or fixed to a cover 38. The cover 38 is longitudinally movably mounted on the casing 12 by means of a locating ring 39, and a spring 40, and forms a trigger for the device 10. Abutting the cover 38 is the shroud 13 which upon movement deflects the cover 38 which in turn moves the actuating member 37 and subsequently the sleeve 35 to release the balls 29.

Accordingly upon the cylinder 16 being released it is forced under the influence of the compressed spring 25 to decrease the variable volume and force the drench out through the passage 21. It should further be appreciated that the balls 29 are retained in a carriage 41 which is mounted on the external surface of the cylinder 16.

The needle of the device 10 is mounted in a support 42, support 42 which is fixed to the left hand end of the piston 15. Additionally the support 42 has a flange 43 which abuts a spring 44 so that the support 42 is biased against a flange 45 on the cylinder 16 to thus support the cover 38 in a non-operative position.

In operation, upon the cylinder 16 being released the pressure within the dose forces the support 42 to move relative to the shroud 13. Thus with the shroud 13 abutting the hide of the animal and the support 42 being moved towards the passage 14, the needle will then project through the passage and beyond the shroud 13 to puncture the hide of the animal.

As can be seen from above the device 10 is designed for automatic operation for both drenching and injecting. To operate the device 10 the dosage volume is set by rotation of the sleeve 23 and the knob 27 is pulled back until the cylinder 16 is secured in position by the balls 29 being located within recess 30. The operator then grips the casing 12 and inserts the needle until the shroud 13 engages the hide of the animal. The user then pushes the shroud 13 towards the animal thereby moving the cover 38 and releasing the cylinder 16. The drench within the variable volume is then forced out through the needle. For non-automatic use the shroud 13 can be removed and the cover 38 manipulated by the operator directly.

It should be appreciated that in the above described preferred embodiment the piston 15 is fixed to the casing 12 and the cylinder 16 is movably mounted. However the relative portions of the piston 15 and cylinder 16 could be reversed so that the cylinder is fixed to the casing 12 and the piston 15 is movable.

What we claim is:

1. An injector comprising, an elongated hollow body, an interacting piston and cylinder mounted within the body and co-operating to provide a variable volume chamber with said piston or cylinder fixed to said body, a first passage extending from said chamber to one end of said body to communicate with an injection needle fixed to the body, a second passage extending from said chamber toward the other end of said body and to be connected to a reservoir of liquid to be delivered by said injector, valve means restricting said liquid to move through said injector from second passage to said first passage, spring means biasing said piston and cylinder to move relative to each other to minimise the volume of said chamber, retaining means to selectively prevent relative movement of said piston and cylinder to minimise said volume, and trigger release means movably mounted at said one end of said body and operatively associated with said retaining means to operate same upon movement of said trigger release means to permit relative movement between said piston and cylinder to thereby eject liquid through said first passage.

2. The injector of claim 1, wherein said piston is fixed to said one end of said body, and said cylinder is movable longitudinally of the body, and the injector further includes a conduit fixed to said cylinder and extending therefrom outwardly of the other end of said body to enable gripping thereof by an operator to move the cylinder relative to the piston to maximise the volume of said chamber, and wherein said first passage extends through said piston, and said second passage extends through said conduit.

3. The injector of claim 1 or 2 wherein said retaining means includes projection means radially movable, relative to the longitudinal axis of said body, between a retaining position preventing said relative movement and a release position allowing said relative movement, and said release means includes a member movable axially of said body from a first position retaining said projection means in the first position thereof, and a second position allowing radial movement of the projection means to the second position thereof, and said trigger release means selectively axially moves said member.

4. The injector of claim 3 wherein said trigger release means is longitudinally movable of the body to move said member.

5. The injector of claim 3 further including a shroud movably mounted at said one end of said body and at least partly covering said needle and adapted to engage said trigger release means to activate same upon forced contact of said shroud with an animal to be injected.

6. The injector of claim 3 wherein said projection means is a plurality of balls and a cage retaining the balls in an angularly spaced relationship about the longitudinal axis of said body, and said cylinder has radially outwardly open recesses on a radially outer peripheral surface of said cylinder within which said balls are located to prevent movement of the cylinder relative to the piston to minimise said volume.

7. The injector of claim 6 further including further spring means biasing said member to the first position thereof.

8. The injector of claim 7 further including dosage adjustment means to adjust the volume of liquid delivered by the injector.

9. The injector of claim 8 wherein said adjustment means is a longitudinally movable adjustment sleeve 3 surrounding said conduit with the longitudinal position thereof defining the maximum longitudinal relative movement between the piston and cylinder.

10. The injector of claim 6, wherein said member is a sleeve co-axial and co-extensive with respect to said cylinder and encompassing said cylinder, said sleeve having a cam surface positioned to engage said balls to move same into said recesses upon movement of said sleeve to a predetermined position relative to said cylinder.

11. The injector of claim 10, further including a spring biasing said sleeve to said predetermined position of said sleeve.

* * * * *